(12) United States Patent
Jamasbi et al.

(10) Patent No.: US 9,080,154 B1
(45) Date of Patent: Jul. 14, 2015

(54) CANCER STEM CELL SURVIVOR LINES

(71) Applicant: BOWLING GREEN STATE UNIVERSITY, Bowling Green, OH (US)

(72) Inventors: Roudabeh J. Jamasbi, Bowling Green, OH (US); Taghreed N. Almanaa, Bowling Green, OH (US); Michael E. Geusz, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 0 days.

(21) Appl. No.: 13/855,694

(22) Filed: Apr. 2, 2013

Related U.S. Application Data

(60) Provisional application No. 61/618,968, filed on Apr. 2, 2012.

(51) Int. Cl.
*C12N 5/09* (2010.01)

(52) U.S. Cl.
CPC .................................. *C12N 5/0693* (2013.01)

(58) Field of Classification Search
CPC ........... A61K 36/9066; A61K 49/0004; A61K 49/0002; A61K 38/00; A61K 51/008; A61K 51/0497; C07C 57/42; C07C 49/255; C07C 49/248; C07C 69/88; G01N 1/00; G01N 33/48; G01N 33/4833; G01N 33/5005; G01N 33/5008; G01N 33/5011; G01N 33/5014; G01N 33/5017; G01N 33/502; G01N 33/5044
See application file for complete search history.

(56) References Cited

U.S. PATENT DOCUMENTS

2010/0316631 A1* 12/2010 Safavy ........................ 424/133.1
2011/0191868 A1* 8/2011 Gupta et al. ...................... 800/8

OTHER PUBLICATIONS

Yan, D. et al. 2012. (Published Dec. 22, 2011).Properties of Lewis Lung Carcinoma Cells Surviving Curcumin Toxicity.Journal of Cancer 3:32-41. specif. p. 33.*
Ye, F. et al. 2012. (Jan. 14). Suppression of esophageal cancer cell growth using curcumin, (-)-epigallocatechin-3-gallate and lovastatin. World Journal of Gastroenterology 18(2):126-135. specif. 126-128.*
Shaw, L.M. Tumor Cell Invasion Assays. Chapter 3.3. Invasion Assay. In: Methods in Molecular Biology, vol. 294. J-L. Guan (Ed.) Publ. Humana Press, Inc. Copyright 2005 Totowa, N.J. p. 101.*
D'Angelo RC, Wicha MS; Stem Cells in Normal Development and Cancer; Prog Mol Bioi Transl Sci; 2010; p. 113-158; vol. 95.
Jamasbi RJ, Stoner GD, Foote U, Lankford TK, Davern S, Kennel SJ; A Monoclonal Antibody to a Carbohydrate Epitope Expressed on Glycolipid and on alpha3beta1 Integrin on Human Esophageal Carcinoma; Hybrid Hybridomics; 2003; p. 367-376; vol. 22 No. 6.
Kang MR, Kim MS, Kim SS, Ahn CH, Voo NJ, Lee SH; NF-KappaB Signaling Proteins p50/p105, p52/p100, ReIA, and IKKepsilon are Over-Expressed in Oesophageal Squamous Cell Carcinomas; Pathology; 2009; p. 622-625; vol. 41 No. 7.
Zhao JS, Li WJ, Ge D, Zhang PJ, Li JJ, Lu CL, Ji XD, Guan DX, Gao H, Xu LY, Li EM, Soukiasian H, Koeffler, HP, Wang XF, Xie D.; Tumor Initiating Cells in Esophageal Squamous Cell Carcinomas Express High Levels of CD44; PLoS One; 2011; e21419; vol. 6 No. 6.
Zhang SJ, Ye F, Xie RF, Hu F, Wang BF, Wan F, Guo DS, Lei T; Comparative Study on the Stem Cell Phenotypes of C6 Cells Under Different Culture Conditions; Chin Med J (Engl); 2011; p. 3118-3126; vol. 124 No. 19.
Lim KJ, Bisht S, Bar EE, Maitra A, Eberhart CG; A Polymeric Nanoparticle Formulation of Curcumin Inhibits Growth, Clonogenicity and Stem-Like Fraction in Malignant Brain Tumors; Cancer Biol Ther; 2011; p. 464-473; vol. 11 No. 5.
Zhang S, Balch C, Chan MW, Lai HC, Matei D, Schilder JM, Yan PS, Huang TH, Nephew KP; Identification and Characterization of Ovarian Cancer-Initiating Cells from Primary Human Tumors; Cancer Res; 2008; p. 4311; vol. 68 No. 11.
Matilainen H, Yu XW, Tang CW, Berridge MV, McConnell MJ; Sphere formation reverses the metastatic and cancer stem cell phenotype of the murine mammary tumour 4T1, independently of the putative cancer stem cell marker Sca-1; Cancer Letters; 2012; p. 20-28; vol. 323.
Ferlay J, Shin HR, Bray F, Forman D, Mathers C, Parkin DM; Estimates of Worldwide Burden of Cancer in 2008 Globocan 2008; International Journal of Cancer; 2010; p. 2893-2917; vol. 127.
Awad O, Yustein JT, Shah P. Gul N, Katuri V, O'Neill A, Kong Y, Brown ML, Toretsky JA, Loeb DM; High ALDH Activity Identifies Chemotherapy-Resistant Ewing's Sarcoma Stem Cells that Retain Sensitivity to EWS-FLI1 Inhibition; PLoS One; 2010; e13943; vol. 5 No. 11.
Dean M, Fojo T, Bates S; Tumour Stem Cells and Drug Resistance; Nat Rev Cancer; 2005; p. 275-284; vol. 5 No. 4.
Sladek NE; Human Aldehyde Dehydrogenases: Potential Pathological, Pharmacological, and Toxicological Impact; J Biochem Mol Toxicol; 2003; p. 7-23; vol. 17 No. 1.
Vasiliou V. Nebert DW; Analysis and Update of the Human Aldehyde Dehydrogenase (ALDH) Gene Family; Human Genomics; 2005; p. 138-143; vol. 2 No. 2.
Prince Me, Sivanandan R, Kaczorowski A, Wolf GT, Kaplan MJ, Dalerba P, Weissman IL, Clarke MF, Ailles LE; Identification of a Subpopulation of Cells with Cancer Stem Cell Properties in Head and Neck Squamous Cell Carcinoma; Proc Natl Acad Sci USA; 2007; p. 973-978; vol. 104 No. 3.
Liu YJ, Yan PS, Li J, Jia JF; Expression and Significance of CD44s, CD44v6, and nm23 mRNA in Human Cancer; World J Gastroenterol; 2005; p. 6601-6606; vol. 11 No. 42.
Mehlen P. Kretz-Remy C, Preville X, Arrigo AP; Human hsp27, *Drosophila* hsp27 and Human aB-crystallin Expression-Mediated Increase in Glutathione is Essential for the Protective Activity of These Proteins Against TNFa-induced Cell Death; EMBO J; 1996; p. 2695-2706; vol. 15 No. 11.

\* cited by examiner

*Primary Examiner* — John S Brusca
*Assistant Examiner* — Sharon M Papciak
(74) *Attorney, Agent, or Firm* — Marshall & Melhorn, LLC

(57) ABSTRACT

A method of determining the relative effectiveness of potential chemotherapeutic agents designed to inhibit neoplasm, growth or metastasis is described. The chemotherapeutic agent may be curcumin. The invention also relates to kits designed to aid in determining the relative effectiveness of potential chemotherapeutic agents. The invention also relates to cancer stem cell survivor lines that can be included in the kits and used in the method.

7 Claims, 7 Drawing Sheets

CANCER STEM CELL SURVIVOR LINES

CROSS-REFERENCE TO RELATED APPLICATIONS

This application is a non-provisional of and, pursuant to 35 U.S.C. §119(e), claims the benefit of, U.S. Provisional Patent Application Ser. No. 61/618,968, filed on Apr. 2, 2012 under 35 U.S.C. §112(b). Application Ser. No. 61/618,968 is hereby incorporated by reference in its entirety to the extent permitted by law.

BACKGROUND OF THE INVENTION

Esophageal cancer is the eighth most common cancer worldwide, and the sixth most common cause of death among cancers [1]. Of the two types of esophageal cancer, adenocarcinoma (EAC) and squamous cell carcinoma (ESCC), 90% are ESCC, with rates increasing significantly in developing countries [2]. Patients suffering from ESCC have low, five-year survival rate, approximately 13% [3]. The prognosis of ESCC is often poor due to lack of effective treatment [4]. As a result of this limitation newer agents and novel approaches are imperative. Of particular interest is the chemotherapeutic application of curcumin, the major active ingredient of turmeric (*Curcumin longa*) [5-8]. Curcumin induces cell death in some cancers, such as gastric and colon cancers [9], human melanoma [10], and lung cancer [1,1] without major cytotoxic effects on healthy cells [12, 13]. Curcumin induces cell death through a variety of mechanisms by targeting pathways acting through a range of transcription factors, membrane receptors, kinases, and cytokines (reviewed by Anand et al. [14]). Therefore, curcumin has a potential treatment value for cancer either alone or in combination with other treatments, namely chemotherapy [15] and radiation treatments [16]. Although it is rapidly degraded and thus may have little effect outside of the digestive tract [17, 18], curcumin could be effective for treating ESCC because of its direct contact with epithelial cells lining the esophagus during ingestion. One possible reason for the poor prognosis of ESCC is the presence of cancer stem cells (CSCs) in the tumor [19,20]. It is believed that CSCs regenerate themselves and differentiate into non-CSCs that constitute most of the tumor volume [21-24]. Furthermore, CSCs tend to resist currently used cancer treatments, specifically chemotherapy and radiation therapy [25-27]. Therefore, the development of effective treatments for cancer should target this cell subpopulation [28]. Interestingly, curcumin with or without 5-fluorouracil and oxaliplatin significantly reduced the number of cells showing CSC-markers in a colon cancer cell line that had survived previous treatment with 5-fluorouracil [29].

Aldehyde dehydrogenase (ALDH) is highly expressed in CSCs, and thus can be used as a potential marker for identifying and isolating CSCs [30-32]. ALDH is a detoxifying enzyme responsible for the oxidation of both intracellular aldehydes such as ethanol and xenobiotic aldehydes such as cyclophosphamide [33, 34]. High ALDH expression could also indicate the aggressiveness, invasiveness, or metastatic capability associated with different cancers [26, 35]. ALDH1A1 is a member of the ALDH family that participates in alcohol metabolism and offers cellular protection against cytotoxic drugs [36]. Immunohistochemistry with a specific antibody has been used to identify human epithelial cells expressing ALDH1A1 [37]. Although ALDH1A1 has been identified in different type of cancer, this marker has not been evaluated in esophageal cancer.

Another marker for CSCs is CD44 (cluster of differentiation 44). CD44 is an integral cell membrane glycoprotein involved in cell-cell interaction [38]. It has been identified in many types of CSCs, including breast cancer cells [39], head and neck cancer [40], and gastric cancer [41]. High CD44 expression has also been shown to be associated with metastatic and invasive capabilities [42]. In this study, the effects of curcumin on six human ESCC lines were evaluated, and the lines were examined for the presence of CSCs using ALDHIAI and CD44 markers. In addition, the characteristics of curcumin-surviving cells and the original untreated cell lines were compared to determine whether CSCs could be targeted by curcumin treatment. By understanding the effects of curcumin on the stem cell subpopulation of tumors, the importance of its effects on cancer outcome could be recognized.

The ESSC and ESCC-S cells are a set of cell lines that can be used as a kit to determine the relative effectiveness of potential chemotherapeutic agents designed to inhibit neoplasm growth or metastasis. The kit will be particularly useful for testing chemotherapeutic agents that are intended to selectively target CSCs. The cell lines have been ranked according to their CSC content and according to their sensitivity to curcumin, a naturally occurring chemical that is reported to act selectively on cancer stem cells. All stages of drug development could rely on this kit for differential evaluation of drug efficacy.

In addition to the features mentioned above, objects and advantages of the present invention will be readily apparent upon a reading of the following description and through practice of the present invention.

SUMMARY OF THE INVENTION

The invention provides for a cell or cell lines that are selected, from an original population of cells, for the ability to survive a concentration of curcumin added to the culture medium. The concentration of curcumin used can be above or equal to 20 µM, 40 µM, or 60 µM. In at least one embodiment, the original population of cells are cancerous, preferably esophageal squamous cell carcinoma cells, even more preferably the original population of cells are selected from the group consisting of: KY-5, YES-1, TE-8, TE-1, KY-10, and YES-2.

Another aspect of the invention is a kit comprising at least one cell or cell line selected, from an original population of cells, for the ability to survive a concentration of curcumin added to the culture medium. The kit may also contain information regarding the LD50 for curcumin for the cell or cell lines included. The kit may also contain information regarding the cancer survivor cell content for the cell or cell lines included. In one embodiment, the kit will contain at least one esophageal squamous cell carcinoma cell or cell line.

Another aspect of the invention is to provide a method of determining the efficacy of therapeutic agents on cancer stem cells by a) providing a cell or cell line containing cancer stem cells; b) gathering a first measurement of amount of cancer stem cells in a cell or cell line; c) treating the cell or cell line with a therapeutic agent; d) gathering a second measurement of amount of cancer stem cells in the cell or cell line; and e) comparing the first measurement to the second measurement. The therapeutic agent may be curcumin or a curcumin derivative. The method may also include a step where the first and second measurements are further compared to the known, comparable measurements for curcumin treated cell or cell lines.

Another aspect of the invention is a method of testing the efficacy of a therapeutic agent on squamous cell carcinoma by: a) providing a cell or cell line of squamous cell carcinoma; b) gathering a first measurement of a factor selected from the group of: growth rate, tumorigenicity in mice, survival of the patient, state of differentiation, cancer stem cell content, and invasiveness; c) treating the cell or cell line with a therapeutic agent; d) gathering a second measurement of factor selected from the group of: growth rate, tumorigenicity in mice, survival of the patient, state of differentiation, cancer stem cell content, and invasiveness; and e) comparing the first measurement to the second measurement.

BRIEF DESCRIPTION OF THE DRAWINGS

Novel features and advantages of the present invention, in addition to those mentioned above, will become apparent to those skilled in the art from a reading of the following detailed description in conjunction with the accompanying drawings summarized as follows.

DETAILED DESCRIPTION OF THE PREFERRED EMBODIMENTS

Figure 1:
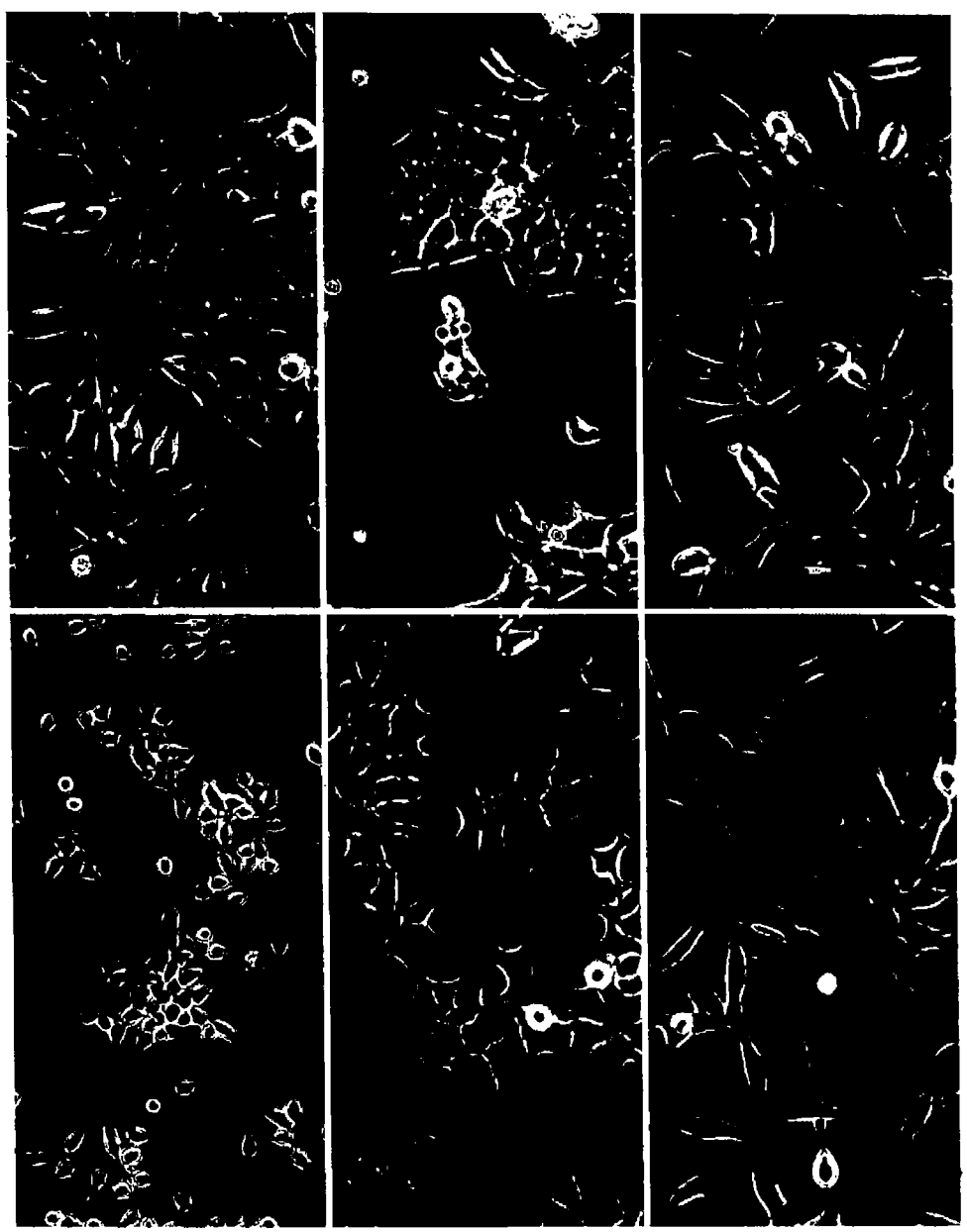
FIG. 1: Morphology of the six ESCC lines. Each of the cell lines had a unique cell shape and size as shown by phase contrast microscopy. Scale bar equals 100 µm.

The preferred system herein described is not intended to be exhaustive or to limit the invention to the precise forms disclosed. They are chosen and described to explain the principles of the invention and the application of the method to practical uses so that others skilled in the art may practice the invention.

Evidence indicates that cancerous tumors depend on a population of cancer cells called cancer stem cells (CSCs) that can regenerate themselves and also change into the other cell types within tumors. CSCs are generally resistant to chemotherapeutic agents and radiation treatments typically used to control cancer growth. CSCs are believed to be the source of cells that proliferate to form a recurring tumor following treatment. Curcumin is an active ingredient of the spice turmeric and has known anti-cancer properties. We have discovered that when six cancer cell lines made from human esophageal squamous cell carcinomas (ESCC lines) are exposed to a high concentration of curcumin, most of the cells die, but the surviving cell lines produced from this treatment have CSC properties that are significantly diminished relative to the original cell lines. These six surviving cell lines (ESCC-S) differ in their percentage of cells with CSC markers such as aldehyde dehydrogenase 1A1 and CD44. Any or all of these twelve cell lines (ESCC and ESCC-S) can be used in combination in a kit to investigate how CSC properties influence cancer cell growth, resistance to cancer treatments, tumorigenesis, and other characteristics important for developing better cancer treatment or prevention strategies. Furthermore, we have developed methods for maintaining two of the ESCC lines as tumorspheres in culture, which are cell clusters composed nearly entirely of CSCs.

MATERIALS AND METHODS

Cell Lines and Culture Conditions

The six human esophageal squamous cancer cell lines (TE-1, TE-8, KY-5, KY-10, YES-1, and YES-2) were obtained from various sources [43-46]. Some of the ESCC lines are available from JCRB: Japanese Collection of Research Bioresources, http://cellbank.nibio.go.jp. The cell lines were cultured in Dulbecco's modified eagle medium (DMEM) supplemented with penicillin (100 units/ml), streptomycin (100 µg/ml), L-glutamine (2 mM) (GIBCO, Invitrogen, N.Y.), and 10% fetal bovine serum (FBS, Summit Biotechnology, Ft. Collins, Colo.). This medium was designated as complete DMEM. The culture cells were maintained in 100-mm tissue culture dishes (Falcon, Lincoln Park, N.J.) at 37° C. in a 100% humidified incubator containing 5% $CO_2$. When the cells reached near confluency, the cells were washed with phosphate buffered saline (PBS) once and incubated with trypsin (Trypsin-EDTA 0.25%, GIBCO, Invitrogen, N.Y.) for two min. After incubation, the cells were washed once with complete DMEM to inactivate trypsin. The cells were then collected by centrifugation at 800×g, resuspended in complete DMEM and plated into new culture dishes.

Morphological Examination

To examine the morphology of the ESCC cell lines, each cultured line was trypsinized, washed and counted using a hemocytometer (Hausser Scientific, Pa.). The cells were then plated into 100-mm dishes ($1 \times 10^5$ cells/plate) in complete DMEM and incubated at 37° C. When the cells reached near confluency, approximately 70-75%, the cultures were photographed using a phase-contrast microscope (Olympus CK40) equipped with a color digital camera (Kodak M575).

Curcumin Treatment

To determine the effect of different doses of curcumin on the ESCC lines, each cell line was plated in 24-well plates (Corning) at a density of $5\times10^4$ cells/well in complete DMEM, and incubated at 37° C. Curcumin (Sigma-Aldrich, St Louis, Mo.) was dissolved in dimethyl sulfoxide (DMSO) to make a stock solution of 20 mM curcumin. For each experiment, stock solution was diluted to the final concentrations (20, 30, 40, 60 and 80 µM) in complete DMEM. Twenty-four hours after plating, the wells were washed with PBS once, and 1 ml of each curcumin dosage was added (4 wells/dosage) and incubated for 30 hrs. Four other wells received complete DMEM or complete DMEM with 0.2% DMSO as controls. The inhibition of cell growth in response to curcumin treatment was assayed with the crystal violet staining assay according to a standard protocol [47]. Briefly, the cells in each well were washed once with PBS, stained with 200 µl crystal violet in 50% ethanol (10 mg/ml), and incubated at room temperature for 10 min. The crystal violet was then removed and the wells were washed two times with distilled water, and 600 µl of 1% sodium dodecylsulfate (SDS) in water was added to each well. The plates were maintained overnight at room temperature on a shaker to dissolve the dye. Absorbance was read at 490 nm using a Wallac Victor 1420 Multilabel plate reader (Perkin Elmer, Waltham, Mass.). The background readings from the SDS solution were subtracted from each reading and the percentage of cells remaining after curcumin treatment was calculated. The results were plotted in OriginPro 7.5 (OriginLab) and analyzed by ANOVA.

Curcumin-Surviving Subpopulations

To select for a curcumin-surviving cell subpopulation, each of the ESCC cell lines was cultured in 100-mm dishes ($1\times10^5$ cells/dish) with complete DMEM and incubated at 37° C. until reaching near confluency, approximately 80%. After incubation, the medium was removed and the cells were incubated in complete DMEM containing either 40 or 60 µM curcumin in dissolved in 0.2% DMSO for 30 hrs. After incubation, the medium-containing curcumin was removed and replaced with complete DMEM to allow cells that survived the treatment to grow. After the surviving cells formed colonies (normally four weeks after treatment), the colonies were counted, trypsinized, and passaged. The cell lines that developed were designated the curcumin-surviving cell lines.

Exposure of the Curcumin-Surviving Cell Lines to Curcumin

To compare the effect of curcumin on the original cell lines and the curcumin-surviving cell lines, the curcumin-surviving lines were cultured in 24-well plates ($5\times10^4$ cells/well) in complete DMEM and incubated at 37° C. Twenty-four hours after plating, each of the four wells was treated with 40 or 60 µM curcumin and incubated for 30 hrs. The inhibition of cell growth in response to curcumin treatment was assayed with the crystal violet staining assay as described above.

Immunocytochemistry

To assess the expression of the stem cell markers ALDH1A1 and CD44 in both the original ESCC cell lines and the curcumin-surviving cell lines, each line was grown on glass cover slips in complete DMEM. After two days, the cover slips were rinsed with PBS and fixed with methanol for 5 min. The cover slips were then washed three times with PBS, exposed to 0.3% hydrogen peroxide for 3 min and rinsed three times with PBS. Next, the cells were blocked with normal goat serum (Rockland, Gilbertsville, Pa.) at 1:100 dilution in PBS for 30 min. The cover slips were then incubated with a primary antibody for 2 hrs. at room temperature, after which the cover slips were washed three times with PBS and incubated with a secondary antibody for 30 min. For ALDH1A1 staining, a rabbit anti-human ALDH1A1 antibody (Anti-ALDH1A1, 15910-1-AP, 133 µg/ml Proteintech Group, Chicago, Ill.) at 1:100 dilution and a goat anti-rabbit antibody conjugated with horseradish peroxidase (Rockland, Gilbertsville, Pa.) at 1:1000 dilution were used. For CD44 staining a mouse antihuman CD44 antibody (BD Biosciences, Franklin Lakes, N.J.) at 1:10 dilution and a goat anti-mouse horseradish peroxidase-conjugated antibody (Sigma-Aldrich, St Louis, Mo.) at 1:40 dilution were used. The cells were then reacted with ImmunPACT DAB (Vector Laboratories, Burlingame, Calif.) for 10 min. The cover slips were washed three times with water, dehydrated in an ethanol series, cleared with Citrosolve (Fisher, Pittsburgh, Pa.), and mounted on glass slides with Permount (Fisher, Pittsburgh, Pa.). Control covers slips did not receive the primary antibody but were otherwise treated identically.

Image Analysis

The images of cell cultures immunostained for ALDH1A1 or CD44 were analyzed with ImageJ (NIH) and OriginLab (Microcal) software. To determine the intensity of staining, all cells were imaged with a 12-bit digital camera (MicroMax, Princeton Instruments) and a Zeiss Axiophot microscope. The images were thresholded identically using a pixel intensity (brightness) value of 500 analog-to-digital units (ADDs). For counting cells, ImageJ was used to identify cells within a normal size range (500-4000 pixels in area) that did not touch the edge of the image.

Enzyme-Linked Immunosorbent Assay (ELISA)

To determine the level of ALDH1A1 and RelA (p65), the major subunit of transcription factor (NF-κB), on both curcumin-surviving cells and original cell lines, ELISA was performed as described previously [48]. Briefly, each cell line was cultured in 96-well plates ($5\times10^4$ cells/well) and incubated for 24 hrs at 37° C. After incubation, the wells were washed once with PBS and fixed with methanol for 5 min; the wells were then washed twice with PBS. Different dilutions of each antibody (anti-p65, Santa Cruz Biotechnology, SC-109, 200 µg/ml, and anti-ALDH1A1, Proteintech Group, 15910-1-AP, 133 µg/ml) were prepared in complete DMEM (1:50, 1:100, 1:200 and 1:500, 1:1000, 1:2000, respectively). The wells were incubated with 100 µl of each dilution (3 wells/dilution) for 2 hrs at 37° C. After incubation, the wells were washed with PBS three times and incubated with 100 µl/well of galactosidase-conjugated goat anti-rabbit secondary antibody (Southern Biotech, Birmingham, Ala.) (1:500 dilution in complete DMEM) for 2 hrs at 37° C. After incubation, the wells were washed with PBS three times and 100 lll/well of substrate solution (1 mg/ml p-nitrophenyl-β-D-galactopyranoside in phosphate buffer, pH 8.0) were added and incubated at 37° C. for one hour in darkness. The development of yellow color indicated a positive reaction. The antigen-antibody reactions were measured by determining the optical density (O.D.) at 410 nm using MR-600 microwell plate reader (Dynatech Lab Inc.). The resulting absorbance was analyzed using ANOVA.

RESULTS

Morphological Characteristics of the ESCC Lines

The characteristics of patients, tumors, and esophageal cell lines derived from each tumor are listed in Table 1. All cell lines grew as adherent mono layers with unique morphological characteristics in size and shape as shown in FIG. 1. The morphological characteristics of the ESCC cell lines were similar to the morphologies that were originally described [43-46].

Cytotoxic Effect of Curcumin on the ESCC Lines

Figure 2:
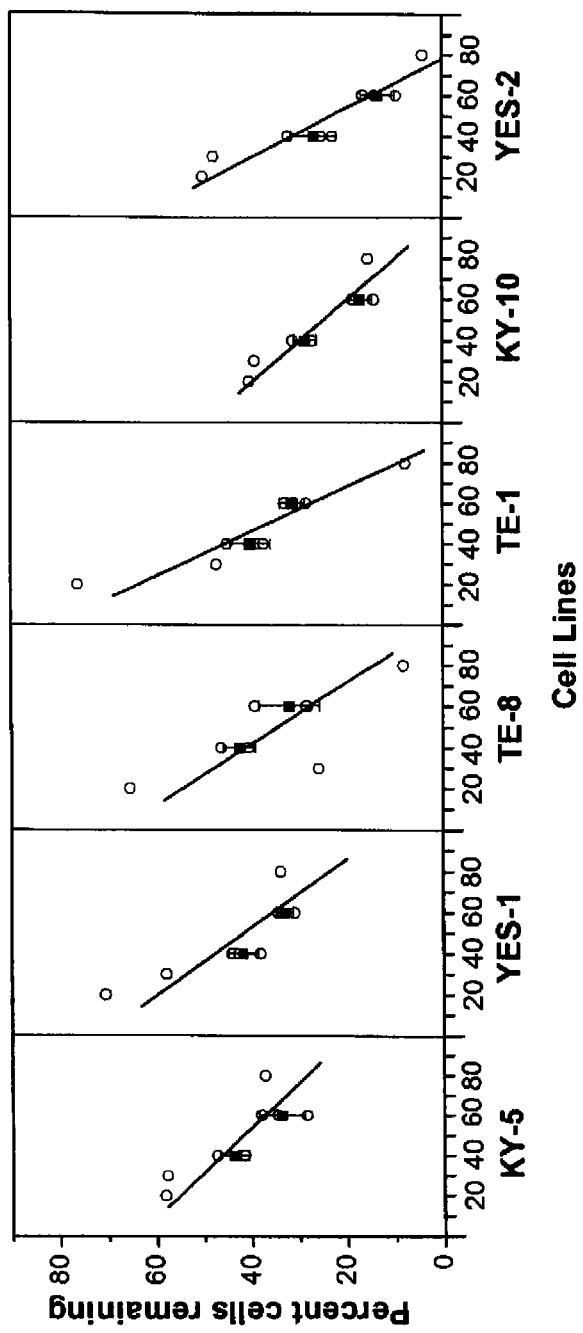
FIG. 2: Percentage of ESCC lines remaining after curcumin treatments. Cell death was measured by a standard crystal violet assay after incubation with 20-80 µM curcumin for 30 hrs. Each point represents effect of one curcumin dosage (20, 30, 40, 60 or 80 µM). For 40 and 60 µM curcumin, the error bar indicates the mean (±SD) from three experiments.

To assess the sensitivity of the six human ESCC lines to curcumin, the cell lines (TE-1, TE-8, KY-5, KY-10, YES-1, and YES-2) were plated in 24-well plates for 24 hrs and then exposed to 20, 30, 40, 60, and 80 μM curcumin and to 0.2% DMSO as a control for 30 hrs. The resulting cell density was determined by standard crystal violet assay. The cell density remaining after the treatment is shown in the dose-response curve (FIG. 2). Curcumin caused a reduction in cells in a dosage dependent manner in all six ESCC cell lines. However, KY-5 had the highest percentage of cells remaining at the highest curcumin concentration, and the YES-2 cell line had the lowest percentage of cells remaining. When the cell lines were ranked from low to high according to their sensitivity to 60 μM curcumin the order was: KY-5, YES-1, TE-8, TE-1, KY-10, and YES-2. The range of the percentage of cells remaining after the curcumin treatment across the six cell lines was 10.9% to 36.3% at 60 μM curcumin.

Comparison of the ESCC Lines and the Curcumin-Surviving Lines

According to the dose-response results, 60 μM curcumin was chosen to select for the curcumin-surviving cell line subpopulations. To establish this subpopulation, $1 \times 10^5$ cells from each ESCC lines were plated into a 100 mm tissue culture dishes and incubated until they reached near confluency. The cells were then exposed to 60 μM curcumin for 30 hrs. and the surviving colonies formed were counted. The number of colonies formed after 60 μM curcumin treatment varied among the six cell lines. The YES-2 cell line did not form any colony at the concentration of 60 μM curcumin, therefore was treated with lower concentration (40 μM) curcumin. The numbers of surviving colonies formed after 60 μM curcumin were 0, 8, 17, 19, 25, and too many colonies to count, for YES-2, TE-1, TE-8, KY-10, YES-1, and KY-5, respectively. The KY-5 cell line had the highest number of surviving colonies whereas the YES-2 cell line did not form any colonies after 60 μM curcumin but formed 15 colonies after treatment with 40 μM curcumin.

To further distinguish between the original ESCC cell lines and the curcumin-surviving lines, we measured NF-κB, ALDH1A1, and CD44 levels along with the effect of curcumin on these lines.

Evaluation of ALDH1A1 and NF-κB Level by ELISA

Figure 3:
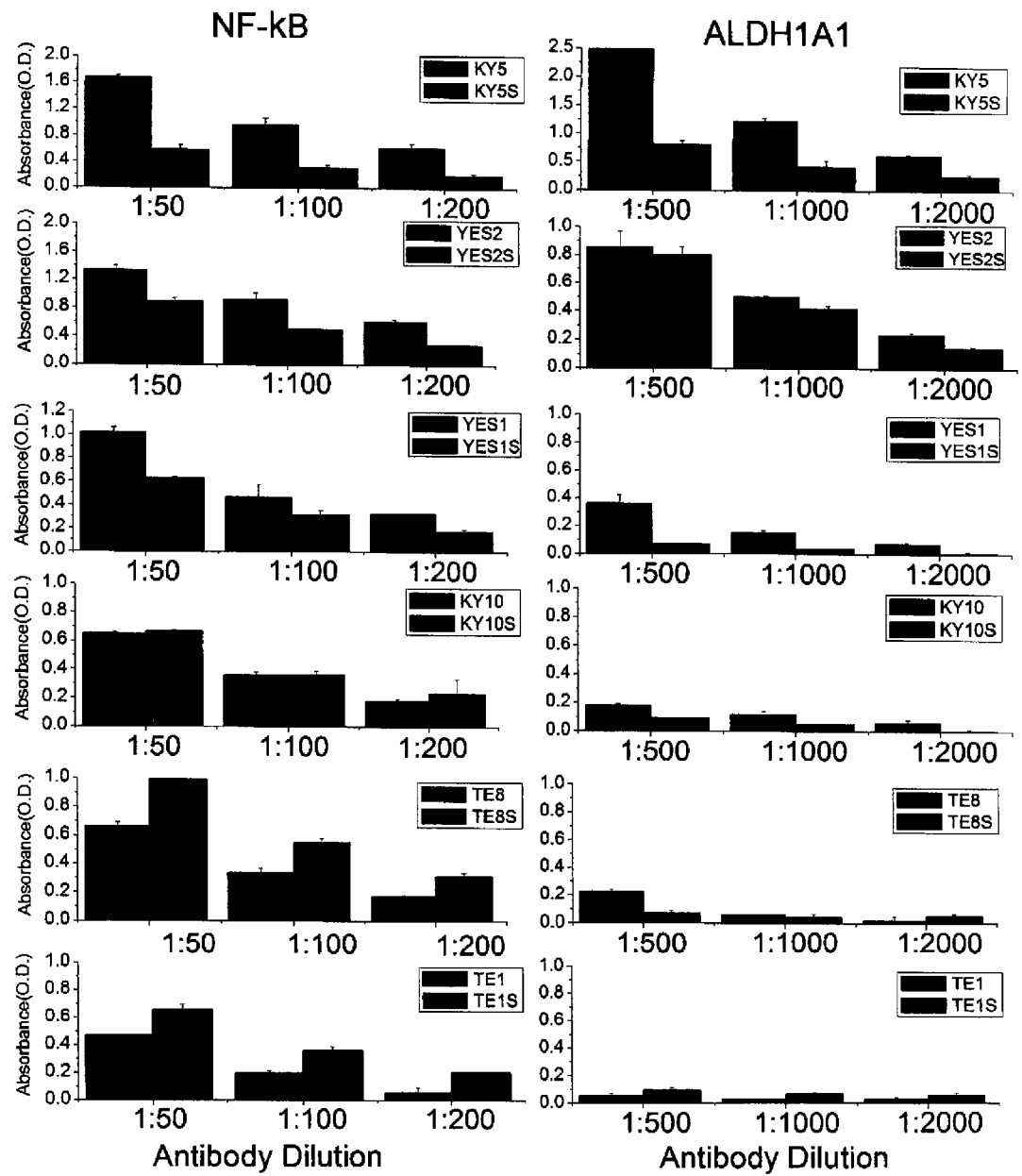
FIG. 3: Evaluation of NF-κB and ALDH1A1 level in ESCC lines and curcumin surviving lines by ELISA. The six cell lines are arranged by their labeling with antibodies towards NF-κB or ALDH1A1 at three dilutions (3 wells/dilution). The results indicate the average optical density at 410 nm of three wells±SD. Curcumin-surviving cell lines were derived from ESCC lines that survived 60 µM curcumin treatments, except YES-2, which survived 40 µM curcumin. Surviving lines are designated with "S".

The ALDH1A1 and NF-κB level were measured by ELISA using the original ESCC cell lines and the curcumin-surviving cell lines. As shown in FIG. 3, the level of ALDH1A1 and NF-KB were detected in all the original ESCC cell lines and the curcumin-surviving cell lines. The cell lines were heterogeneous with respect to ALDH1A1 and NF-κB levels. The KY-5 cell line showed the highest ALDH1A1 and NF-κB levels whereas the TE-1 cell line showed the lowest level of both markers. The results also showed that the curcumin surviving lines had lower ALDH1A1 level compared to the original cell lines (t-test, p<0.005). In addition, the results also showed that the KY-5, YES-1 and YES-2 curcumin surviving lines had lower NF-κB levels when compared with the original cell lines (t-test, p<0.005). However, the TE-1 and TE-8 curcumin-surviving lines showed an increase of NF-κB level and the KY-10 curcumin-surviving cell lines showed no difference between the original cell line and the curcumin-surviving cell line (t-test, p>0.05), indicating a heterogeneity of these lines.

Assessment of ALDH1A1 Expression in ESCC Lines

Figure 4:
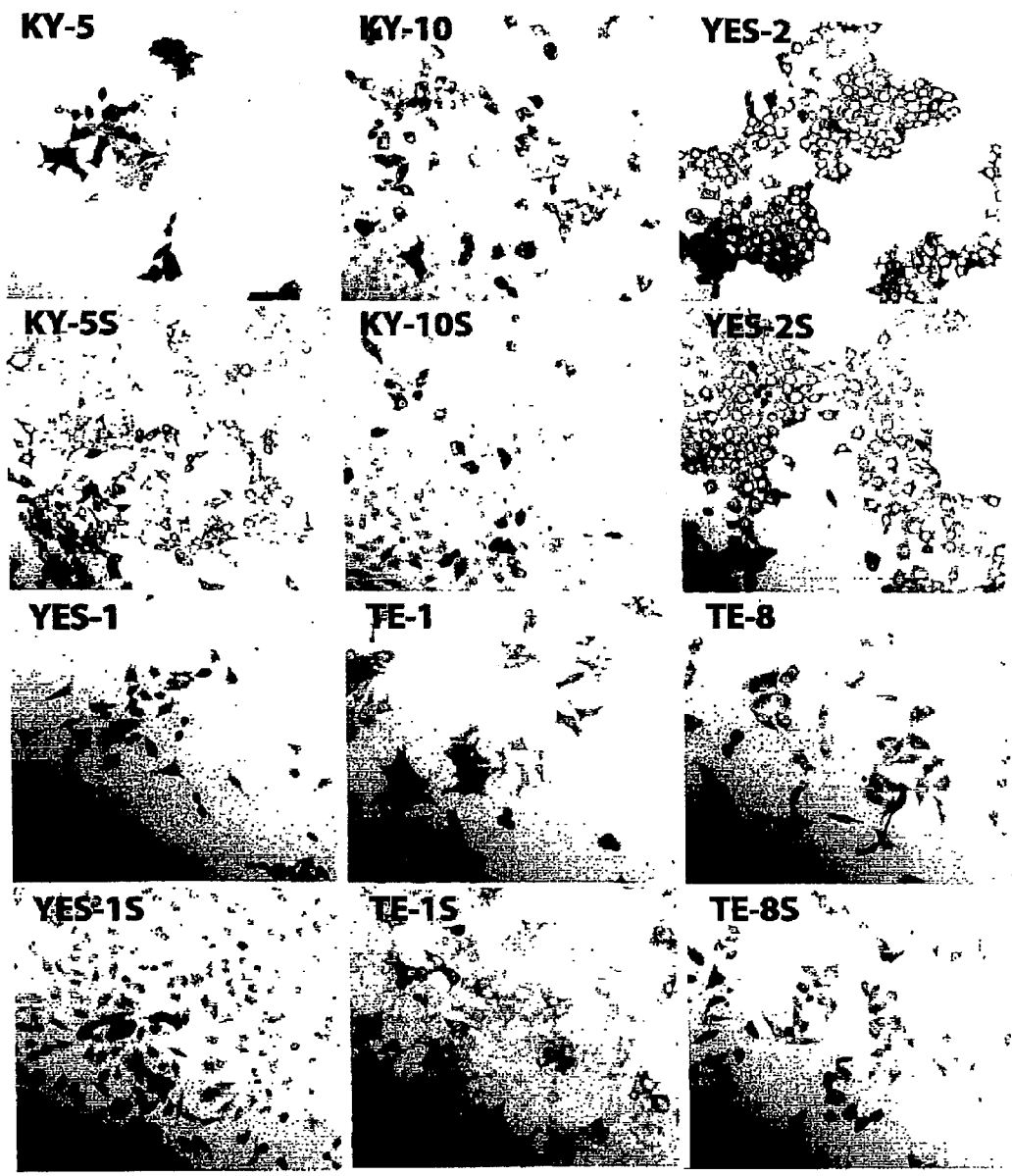
FIG. 4: ALDH1A1 immunocytochemistry. After immunostaining for ALDHIAl, all six ESCC lines and curcumin-surviving lines show distinct high and low-staining cells. Cells were grown on glass cover slips and stained 48 hr. after plating. "S" indicates the curcumin surviving cell lines.
Figure 5:
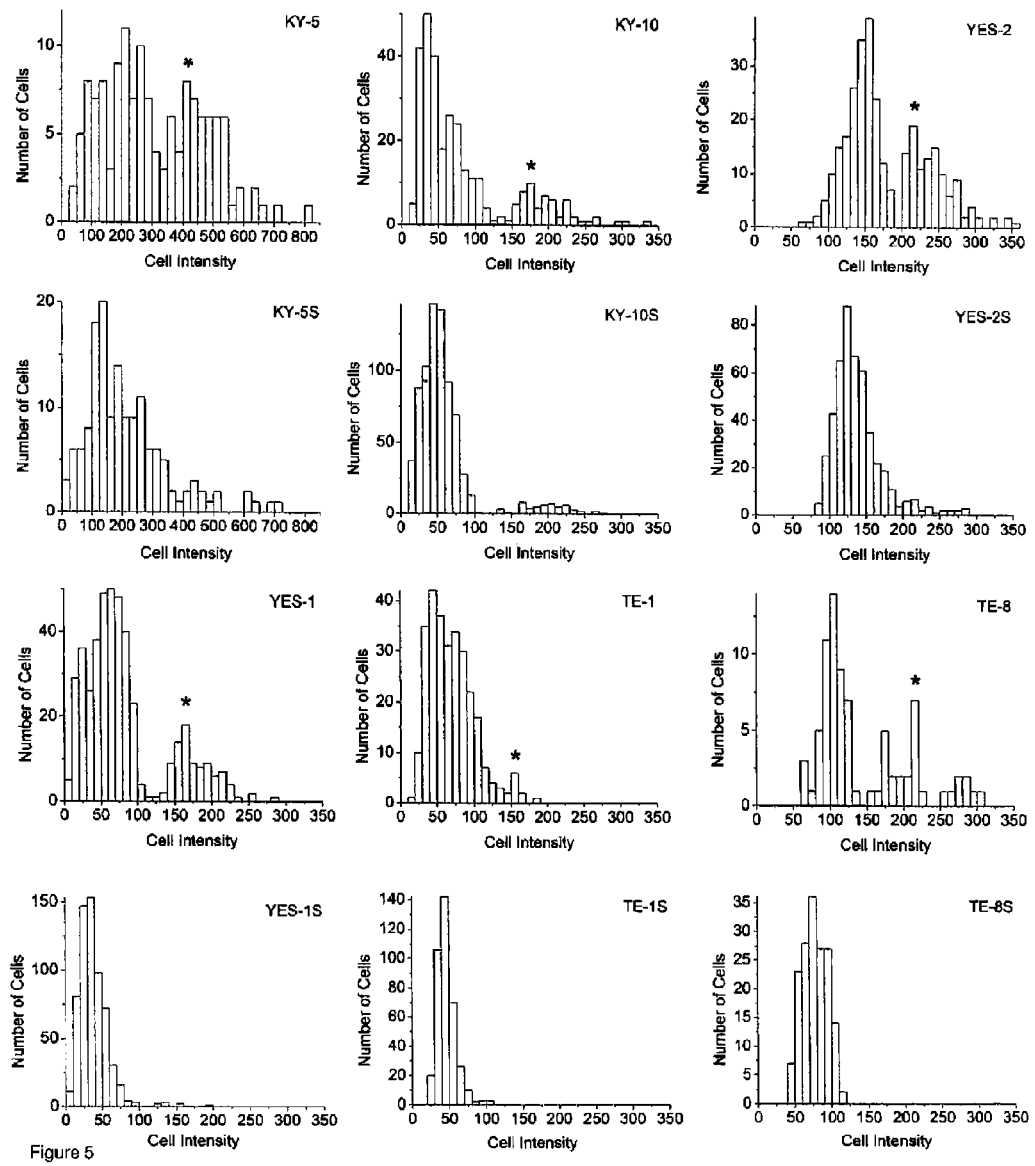
FIG. 5: Histograms evaluate the ALDH1A1 antibody staining of the ESCC lines and curcumin-surviving lines. Histograms summarizing results of ALDH1A1 immunocytochemistry shown in FIG. 4. The maximum of the high-staining subpopulation is shown by "*" in each of the original cell lines. The curcumin-surviving cell lines, indicated with "S", had a significant loss of the high-staining subpopulation.

ALDH1A1 has been used to detect cancer stem cells in different types of human cancer using immunostaining [35, 49]; however, the expression of the ALDH1A1 in human esophageal cancer has not been studied. To address this question, the expression of ALDH1A1 was examined in the six ESCC lines using rabbit anti-human ALDH1A1 antibody. As shown in FIG. 4, high ALDH1A1 staining-cell was detected in the cytoplasm of the six cell lines. All cell lines were heterogeneous with respect to the ALDH1A1 staining, revealing two subpopulations within each line, high and low ALDH1A1 staining. The intensity of staining was at least two times higher in the high staining subpopulation (FIG. 5). The percentage of cells with high ALDH1A1 staining was analyzed based on counts of individual high and low-staining cells. The percentage of cells with high ALDH1A1 staining ranged from 11.3% to 55.7%. KY-5 showed the greatest percentage of highly stained cells, whereas TE-1 showed the lowest.

Detection of ALDHIAI Positive Cells in the Curcumin-Surviving ESCC Cell Lines

Multiple studies have demonstrated that invasion and metastasis are mediated by a cellular component that displays high ALDH1 activity [26,50], suggesting that ALDH1A1 can be a significant target for cancer therapy. Therefore, the expression of ALDH1A1 in the curcumin-surviving cell lines was evaluated to test for any effect of curcumin on ALDH1A1 expression that is transmissible through cell division and how this property may differ among the cell lines. Like the original cell lines, the curcumin-surviving lines had high and low subpopulations of ALDH1A1-staining cells. Interestingly, each of the curcumin-surviving cell lines showed a significant loss in mean staining intensity when compared to their corresponding original cell line (ANOVA, F=457.06, p<0.001). This decline is visible as a loss of nearly all of the high-staining subpopulations (FIG. 5). TE-8 showed complete loss of its high-staining population. As in the original lines, staining intensity was at least two times higher in this subpopulation considered to be CSCs (FIG. 5). The percentage of high ALDH1A1-staining cells in the curcumin-surviving lines ranged from 0 for TE-8S to 19% for KY-5S.

Detection of CD44-Expressing Cells in ESCC and Curcumin-Surviving Lines

Figure 6:
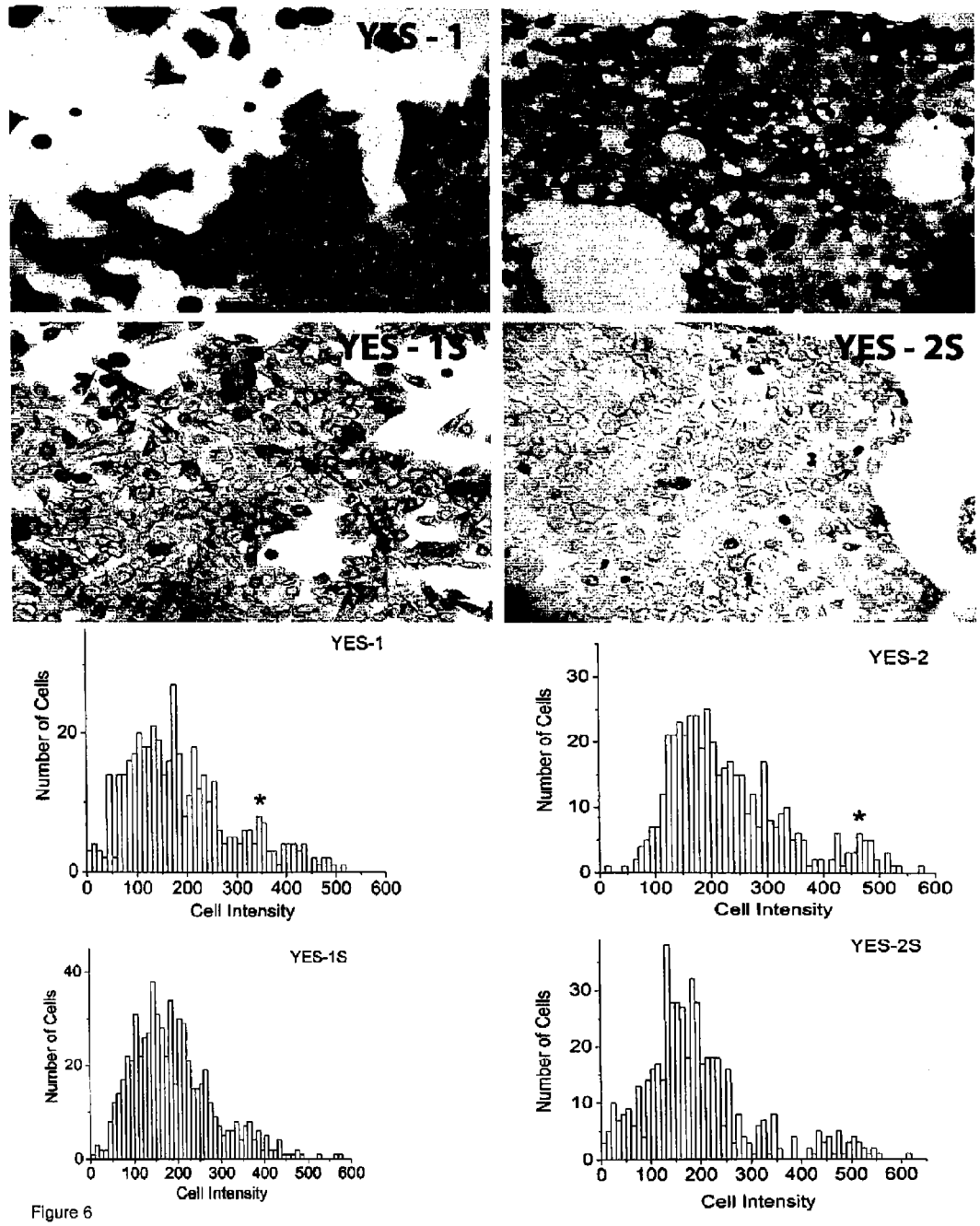
FIG. 6: CD44 immunocytochemistry. Above: two of the six ESCC lines, YES-1 and YES-2, and their curcumin-surviving lines, YES-1S and YES-2S, following immunostaining against CD44. Below: histograms showing a high-staining subpopulation in each of the original cell lines (peak marked by "*") that is diminished in the surviving lines.

CD44 has been used to identify cancer stem cells in different types of human cancers [39-41] including ESCC [51]. An antibody to CD44 was used with two of the original ESCC lines, YES-1 and YES-2, and their curcumin-surviving lines (YES-1S and YES-2S). YES-1 and YES-2 were the two lines with the highest ALDH1A1 expression. As shown in FIG. 6, CD44-stained cells were detected in all four lines and these cells comprised a distinct subpopulation. The percentage of high-staining cells was 19% and 16% for YES-2 and YES-1, respectively. The percentage of high CD44-staining cells was lower in the curcumin surviving cell lines—9.2% and 6.5% for YES-2S and YES-1S, respectively. (ANOVA, F=18.6, p<0.000)

Effect of Curcumin Treatment on the Curcumin-Surviving Lines

Figure 7:
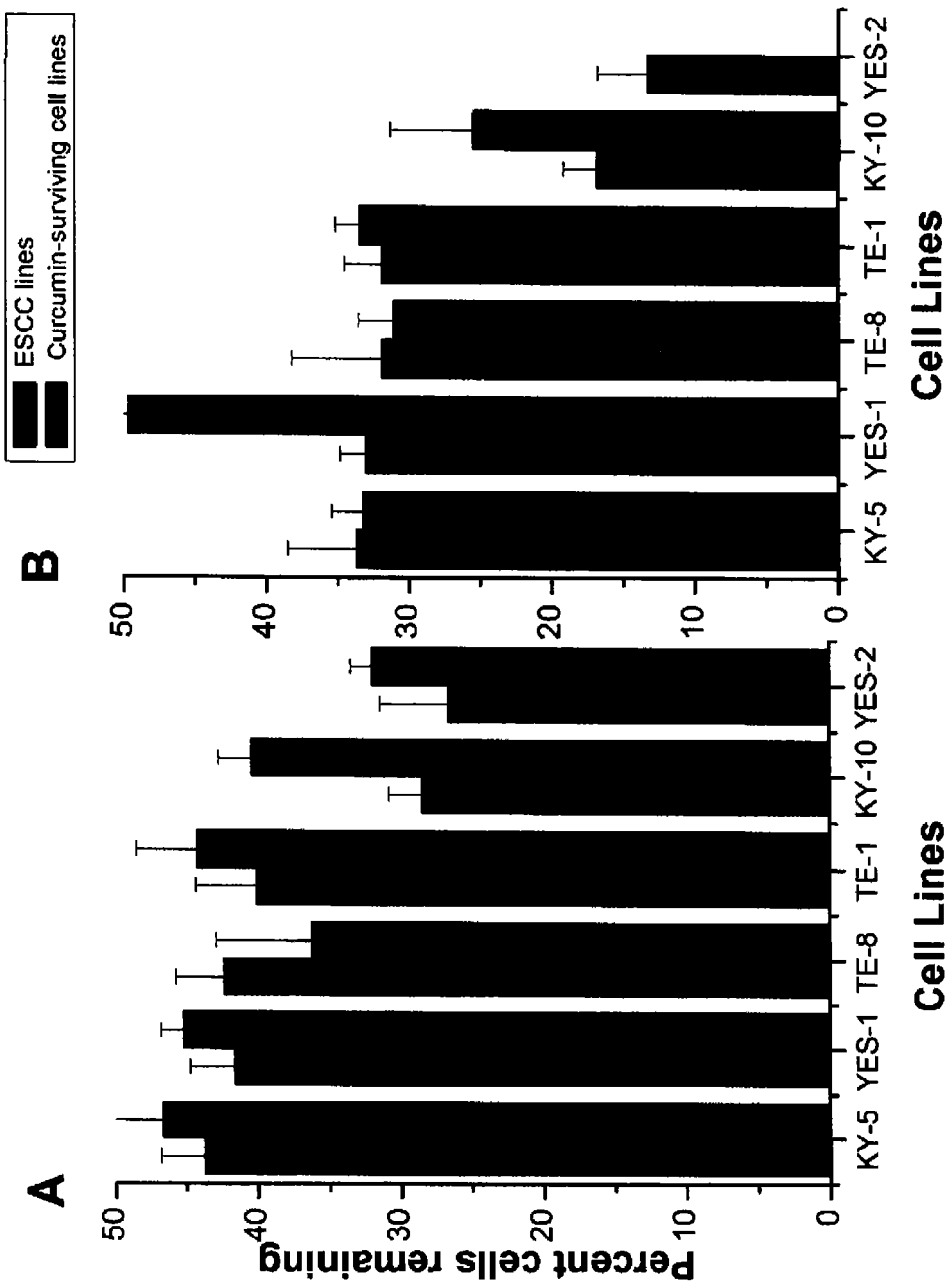
FIG. 7: Cells remaining after treating ESCC cell lines and curcumin-surviving lines with curcumin. Overall, the surviving lines showed a small but significant increase in survivorship to (A) 40 µM and (B) 60 µM curcumin administered for 30 hrs. Data for the original lines are the same as in FIG. 2. The cell lines are arranged by the response of the original lines to 60 µM curcumin. Each bar indicates the average of three experiments±SD.

To compare the effect of curcumin on the ESCC lines and curcumin-surviving lines, the curcumin-surviving cell lines were passaged four times and treated with 40 or 60 μM curcumin. The resulting cell density was determined by standard crystal violet assay and the percentage of cells remaining after treatment was calculated for each line (FIG. 7). This experiment was repeated three times. A two-way ANOVA revealed a small but significant increase in resistance in the curcumin-surviving cell lines relative to the original lines when tested with either of the two curcumin concentrations (factor 1; 40 μM: F=5.132, p=0.0311; 60 μM: F=8.358, p=0.00803; Scheffe post hoc test). YES-1S showed the greatest change from its original cell line. The cell lines also differed significantly from each other in their ability to survive the curcumin treatments (factor 2; 40 µM: F=9.508, p<0.001; 60 µM:
F=12.71, p<0.001; Scheffe).

DISCUSSION

Esophageal cancer is a highly aggressive malignant disease resulting in low patient survival. Because of the poor success rate of standard therapies, innovative approaches for treatment have been tested, and two studies have examined whether curcumin could be a potential candidate for esophageal cancer treatment. In one study, Hartojo et al. [52] examined the effects of curcumin on the NF-κB activity and cell viability of esophageal adenocarcinoma (EAC) and also in combination with 5-fluorouracil (5-FU) and cisplatin. In the other study, O'Sullivan-Coyne et al. [53] investigated the effect of curcumin-induced apoptosis on esophageal cancer cells. In the present investigation, we selected six esophageal squamous cell carcinoma lines to evaluate their sensitivity to curcumin. The six cell lines were found to be similar morphologically to what was shown in the original publications introducing these lines [43-46] (FIG. 1, Table 1).

When the cell lines were treated with curcumin (20-80 µM) for 30 hrs. there was a reduction in cell number in all lines in a dose-dependent manner, consistent with studies using other cell lines, breast, lung, and colorectal (reviewed by Anand et al. [14]), including esophageal cancer cell lines (OE19, OE33, OE21, KYSE450) [53]. We found a significant difference in the response of the lines to curcumin according to the crystal violet assay. The KY-5 cell line, for example, had 37% cells remaining, whereas the YES-2 cell line had only 4% attached cells after 80 µM curcumin. This distinction among the lines was also evident according to the $LD_{50}$ values, which ranged from 32 µM for KY-5 to 15 µM for YES-2 and less than 10 µM for KY-10 (FIG. 2).

Because of the observed variation among the cell lines in response to curcumin, we sought properties that were possibly responsible for this result such as indicators of the relative aggressiveness or resilience of the cells. When we examined two properties associated with cell survival and resistance to chemotherapy, NF-κB and ALDH1A1, we found that these markers also varied among the cell lines. The relative levels of RelA (p65), a major subunit of the NF-κB transcription factor, varied among the six lines with the highest amount correlated with the lowest sensitivity to curcumin, as exemplified by KY-5 versus TE-1 (FIG. 3). Whereas most studies measure the activity of the NF-κB signaling pathway, such as nuclear entry of RelA, we determined the level of RelA in the ESCC lines. Several studies have shown that the level of NF-κB in cells is correlated with aggressiveness [54, 55], lack of differentiation [56, 57], and resistance to chemotherapy [58]. Kang et al. [54] reported that RelA was expressed more strongly and regularly in ESCC tissues than in normal esophageal tissues. Additionally, Tian et al. [55] reported that two ESCC cell lines (Eca109 and EC9706) showed high p65 expression, and the sensitivity of these cell lines to a chemotherapeutic agent increased after p65 expression was inhibited by p65 siRNA transfection. Zhang et al. [56] reported that the expression level of NF-κB was higher in poorly or moderately differentiated lung cancer cells than in well-differentiated cancer cells. Yu et al. [57] also found that the density of RelA-positive cells was significantly increased in the transition from normal mucosa to adenoma and to adenocarcinoma in colorectal cells. Hatata et al. [58] reported that high NF-κB level in two ESCC cell lines was associated with poor sensitivity to 5-fluorouracil. The variation in NF-κB level we found among the six ESCC lines could indicate differences in the degree of aggressiveness and degree of resistance to chemotherapy.

The other property that may be involved in the variation among cell lines in response to curcumin is the stem cell marker ALDH1A1 that offers cellular protection against cytotoxic drugs [59]. High ALDH1A1 expression was detected in the six ESCC cell lines, but there was considerable variation among the lines (FIG. 4). Our results are consistent with previous studies identifying ALDH1A1 as a stem cell marker in other cancer cell lines [49, 60, 61]. This is the first report to analyze ALDH1A1 expression in ESCC lines. Across the six lines, ALDH1A1 expression was inversely correlated with sensitivity to curcumin, as exemplified by KY-5 versus TE-1 (FIG. 3). Because one of the functions of ALDH1A1 is to protect against cytotoxic agents, the higher ALDH1A1 found in cells with lower sensitivity to curcumin suggests that ALDH1A1 could be protecting against curcumin's effects. Furthermore, the relative ALDH1A1 expression across the lines as determined by anti-ALDH1A1 immunocytochemistry agreed with the ELISA results, as shown in FIGS. 3 and 5. Similarly, the two cell lines with high ALDH1A 1 and NF-κB levels, KY-5 and YES-1, were the least sensitive to curcumin, whereas the more sensitive lines (KY-10, TE-1, TE-8) had lower expression of these two markers. This result supports NF-κB as a marker for cancer stem cells in addition to an indicator of aggressiveness.

Several reports have described effects of curcumin on cancer cell lines (reviewed by Anand et al. [14]), but this is the first study to characterize curcumin-surviving cell lines. All six curcumin-surviving cell lines had lower levels of ALDHIAI when compared with each corresponding original line, based on ELISA and immunocytochemistry. Similarly, NF-κB levels decreased among the three surviving cell lines that had the highest initial levels of NF-κB (KY-5, YES-1 and YES-2) according to ELISA. However, the other three lines showed the same (KY-10) or more NF-κB expression (TE-1 and TE-8) in the surviving lines, and this result was confirmed using immunocytochemistry with the same three lines (TE-1, TE-8, KY-10, data not shown). This distinction between NF-κB and ALDH1A1 when used as stem cell markers could result from the differences between their functions. For example, ALDH1A1 is an enzyme, whereas NF-κB is a cell signaling molecule and transcription factor that serves in multiple cellular pathways. This difference suggests that ALDH1A1 may be a better indicator of stem-like cells.

Interestingly, YES-2 differed from the other lines. While it had high NF-κB and ALDH1A1 expression, it showed more sensitivity to curcumin and was the only line that had no survivors after the 60 µM curcumin treatment. It is not clear why the YES-2 cell line behaved differently, and it should be investigated further. Notably, YES-2 is the only line reported to have metastasized in a patient [62].

Expression of CD44, a stem cell marker, was examined in two of the lines, YES-1 and YES-2, and in their curcumin-surviving lines. These original cell lines were chosen because they had high ALDH1A1 expression. Two subpopulations of cells were recognized in these lines, one with high and one with low CD44 immunostaining. The intensity was two times greater in the high staining cells than in the low staining cells. However, the percentage of highly stained cells was less than what was observed in the ALDH1A1 experiment. The percentage of highly ALDH1A1 stained cells was 36% and 21% for YES-2 and YES-1, respectively whereas the percentage of highly stained CD44 cells was 19% and 16% for YES-2 and YES-1, respectively. One way to explain why the high-staining CD44 subpopulation was smaller than the high-staining ALDH1A1 subpopulation is that the first group contains mostly CSCs, whereas the second group includes other cells. These other cells may include progenitor cells derived from CSCs that are not fully differentiated but continue to express substantial amounts of ALDH1A1 [63].

It is generally believed that cancer stem cells (CSCs) are more numerous in tumors after chemo- and radiation therapy because they are more resistant than non-stem cells, which along with their greater aggressiveness makes them a likely source of tumor recurrence [64-66]. In contrast to standard therapies, we found the high ALDH1A1 and CD44 subpopulations were diminished in the curcumin-surviving lines, suggesting that cell populations surviving curcumin contain fewer stem-like cells.

Because it appeared that we had selected for cells that were intrinsically more resistant to curcumin, we predicted that the surviving lines would be considerably less sensitive to curcumin than the original lines. Although one surviving cell line (YES-1S) showed substantially greater resistance to curcumin, the overall resistance after having been exposed to curcumin was significant but small when all of the lines were examined (FIG. 7). If the sensitivity of each line to curcumin depends, at least in part, on its proportion of CSCs to non-CSCs, then the loss of CSCs in the surviving cell lines, as shown by the immunostaining for stem cell markers, suggests that curcumin sensitivity decreases as the proportion of CSCs declines. However, when comparing across the original six lines, a decrease in sensitivity to curcumin was correlated with increasing stem-like characteristics, as epitomized by KY-5. One explanation for this apparent contradiction is that the range of sensitivity to curcumin detected across the lines could depend on genetic differences among the lines rather than CSC content. In support of this explanation, the surviving lines appear in roughly the same order of sensitivity to curcumin as the original lines despite having lost most or nearly all of their CSCs, as identified by the number of cells with high ALDH1A1 or CD44 levels.

The specific mechanism causing the reduction in stem cells by curcumin was not examined in this study, but we can consider two possibilities. First, the curcumin may have selectively destroyed the CSCs. Second, curcumin may have caused the CSCs to differentiate more frequently into non-CSCs, similar to what has been described in PCC4 embryonal carcinoma cells [67]. The surviving population would, in either case, contain proportionately fewer CSCs. In agreement with the second scenario, CSCs divide symmetrically, forming new CSCs, as well asymmetrically, generating non-CSCs. Curcumin may have altered the balance between these processes. It has been argued that the cell culture environment used with cancer cells can determine the percentage of CSCs present [68]. If the microenvironment of tumors also plays a major role in determining the CSC versus non-CSC composition, then curcumin treatments may improve patient outcome and survivorship by acting on CSCs. The surviving cell lines may have also changed while in cell culture during the few passages before they were tested with the second curcumin treatment. Nevertheless, it is apparent that curcumin reduced the stem cell properties of the lines by either targeting CSCs or by inducing a change in CSCs resulting in cells with reduced stemlike properties.

In agreement with both of these possible mechanisms, researchers have shown that curcumin can modulate or eliminate a variety of cellular targets in cancer cells [69, 70]. Nautiyal et al. [71] reported that a combination of curcumin and the chemotherapeutic agent dasatinib eliminates mRNA stem cell markers, specifically ALDH, CD44, CD133 and CD166 that are enriched in the chemo-resistant colon cancer cells. Also, Yu et al. [29] found that treatment of two colon cancer cell lines that survived FOLFOX (5-FU plus oxaliplatin) with either curcumin alone or in combination with FOLFOX diminished the CSCs markers, CD44 and CD166. Similarly, Fong et al. [72] reported that curcumin decreased the side population associated with stem cell populations in the C6 glioma cell line, as determined by negative Hoechst 33342 nuclear staining. Lim et al. [73] also reported that nanoparticle-encapsulated curcumin used to treat glioblastoma and medulloblastoma cells reduced the number of CD133-positive stem-like cells. Finally, Kanwar et al. [74] reported that difluorinated-curcumin (CDF), a novel curcumin analog, together with other chemotherapeutic agents reduced the CSCs cell markers CD44 and CD 166 in chemo-resistant colon cancer cells. Our results provide evidence that curcumin alone can reduce the stem-like cells in ESCC lines.

Conclusions

The present study demonstrates that curcumin reduces the number of ESCC cells in a dose-dependent manner. By comparing the six ESCC lines the results showed that ESCC cells vary considerably based on CSC properties and sensitivity to curcumin. This study is the first to establish and characterize curcumin-surviving subpopulations among ESCC cells.

By comparing the original ESCC lines and the curcumin-surviving lines we found that the curcumin-surviving cell lines contain fewer stem-like cells than the original lines. These data support clinical applications for curcumin as a chemotherapeutic agent against cancers, particularly ESCC, rather than only as a preventative dietary supplement. Contrary to other chemotherapeutic agents, we predict that the cells that comprise a recurrent esophageal tumor after curcumin treatment would contain fewer CSCs than the original tumor. Because CSCs are considered aggressive and more metastatic, a tumor developing after curcumin treatment may be managed more easily than traditionally treated cancers.

One application of the invention is to distinguish curcumin-type chemotherapy treatments from traditional treatments. Whereas CSCs survive many traditional chemotherapeutic treatments, CSCs are killed by curcumin. Curcumin derivatives have been developed to further improve curcumin's effects, and the ESSC/ESSC-S kit could be used to evaluate their relative effectiveness. In this case, the 12 lines (ESCC and ESSC-S) would be placed in rank order according to their LD50 for curcumin. The LD50 is the concentration that kills half the cells and is used as a measure of drug potency. The candidate drug would be evaluated by comparing its effects on the cell lines with the rank order effects of curcumin. The kit covers a wide range of LD50 values for use in screening candidate anticancer drugs that work like curcumin.

Another application will be to screen candidate drugs for their efficacy against CSCs. If instead it is desirable to screen drug candidates according to their ability to kill CSCs or cause them to differentiate into less aggressive cells, then the cell lines will be rank ordered according to their CSC content. This ranking was determined by experiments as described above that used antibodies against stem cell markers and measurements of cell fluorescence following administration of the stem cell reagent Aldefluor (Stem Cell Technologies). The ability to form clusters of CSCs (tumorspheres) was also demonstrated using ESCC lines. Tumorsphere formation is a defining characteristic of CSCs. Because each of the six original ESCC lines was derived from a different patient, variations in drug response could arise because of genetic differences between these individuals. This source of noise can be minimized by comparing the effectiveness of the drug against each original line with the effect on its corresponding ESCC-S line, which has a lower CSC content. A drug that selectively kills CSCs would show a higher LD50 when used against the ESCC-S line.

A third application is to investigate the role of CSCs in cancer. Changes in CSC content may explain why some tumors expand in size, metastasize to other areas of the body or return after chemotherapy. The cell lines in the kit differ in their CSC content and genetic background. They can be used in basic research studies that include standard in vitro assays to determine cancer cell invasiveness, their ability to form tumors in mice, and how CSC content can be altered in cell lines and tumors. The ESCC and ESCC-S lines would be tested according to their CSC content, and ESCC lines can be compared with their corresponding ESCC-S line to minimize effects from genetic variation. Studies could examine agents that cause differentiation of CSCs, leading to less aggressive cells, or ones that interfere with the maintenance of CSCs in the undifferentiated state.

A fourth application is to test the relative efficacy of any drug treatment against a range of human esophageal cancer cells. In this case, the ESCC lines would be ranked according to their growth rate, tumorigenicity in mice, survival of the patient, state of differentiation (CSC content), or invasiveness as determined by a standard in vitro assay. The kit would provide a battery of well characterized human cells to selectively screen candidate treatments against squamous cell carcinoma. A wide range of data is available on the six ESCC lines from published reports and research by the inventors, as shown in Table 1.

TABLE 1

Reported characteristics of cell lines derived from esophageal squamous cell carcinomas.

| | | | Cell Line Properties | | | |
|---|---|---|---|---|---|---|
| | Patient | | Cell | | | |
| Cell Line | Age | Tumor Differ- entiation | doubling time (hrs) | Tumor- igenicity | Morph- ology | References |
| KY-5 (KYSE-50) | 58 | Poor | 28.2 | Yes | Growing as cluster with smaller in the | Shimada Et al.1991 |
| KY-10 (KYSE110 | 63 | Poor | 19.1 | Yes | Spindle shape | Shimada Et al. 1991 |
| YES-1 | 50 | Poor | 35.2 | Yes | Polygonal to spindle shape | Nakamura 1990 |
| YES-2 | 81 | Moderate | 23.7 | Yes | Polygonal Epithelial shape | Nakamura et al. 1994 |
| TE-1 | 58 | Well | 27.2* | Yes | Spindle shape | Nishihira et al. 1992 |
| TE-8 | 63 | Moderate | 25.7* | N.A. | Spindle shape | Nishihira et al. 1992 |

All tumors were from male patients. Cell line tumorigenicity was determined by subcutaneous injection into nude mice.
N.A.: not available.
*Doubling time was determined in the present study.

REFERENCES

Additional background for the invention is provided by the following references which are hereby incorporated by reference to the extent permitted by law.
1. Ferlay J, Shin H R, Bray F, Forman D, Mathers C, Parkin D M: Estimates of worldwide burden of cancer in 2008: GLOBOCAN 2008. *Int J Cancer* 2010, 127(12):2893-2917.
2. Jemal A, Bray F, Center M M, Ferlay J, Ward E, Forman D: Global cancer statistics. *CA Cancer J Clin* 2011, 61(2):69-90.
3. Kim T, Grobmyer S R, Smith R, Ben-David K, Ang D, Vogel S B, Hochwald S N: Esophageal cancer—the five year survivors. *J Surg Oncol* 2011, 103(2):179-183.
4. Huang D, Gao Q, Guo L, Zhang C, Jiang W, U H, Wang J, Han X, Shi V, Lu S H: Isolation and identification of cancer stem-like cells in esophageal carcinoma cell lines. *Stem Cells Dev* 2009, 18(3):465-473.
5. Cheng A L, Hsu C H, Un J K, Hsu M M, Ho V F, Shen T S, Ko J Y, Un J T, Un B R, Ming-Shiang W et al: Phase I clinical trial of curcumin, a chemopreventive agent, in patients with high-risk or pre-malignant lesions. *Anticancer Res* 2001, 21(4B):2895-2900.
6. Lopez-Lazaro M: Anticancer and carcinogenic properties of curcumin: considerations for its clinical development as a cancer chemopreventive and chemotherapeutic agent. *Mol Nutr Food Res* 2008, 52 Suppl 1:S103-127.
7. Shishodia S, Chaturvedi M M, Aggarwal B B: Role of curcumin in cancer therapy. *Curr Probl Cancer* 2007, 31(4):243-305.
8. Basile V, Ferrari E, Lazzari S, Belluti S, Pignedoli F, Imbriano C: Curcumin derivatives: molecular basis of their anti-cancer activity. *Biochem Pharmacol* 2009, 78(10):1305-1315.
9. Moragoda L, Jaszewski R, Majumdar A P: Curcumin induced modulation of cell cycle and apoptosis in gastric and colon cancer cells. *Anticancer Res* 2001, 21(2A):873-878.
10. Bush J A, Cheung K J, Jr., U G: Curcumin induces apoptosis in human melanoma cells through a Fas receptor/caspase-8 pathway independent of p53. *Exp Cell Res* 2001, 271(2):305-314.
11. Radhakrishna Pillai G, Srivastava A S, Hassanein T I, Chauhan D P, Carrier E: Induction of apoptosis in human lung cancer cells by curcumin. *Cancer Lett* 2004, 208(2):163-170.
12. Chainani-Wu N: Safety and anti-inflammatory activity of curcumin: a component of tumeric (*Curcuma longa*). *J Altern Complement Med* 2003, 9(1):161-168.
13. Syng-Ai C, Kumari A L, Khar A: Effect of curcumin on normal and tumor cells: role of glutathione and bcl-2. *Mol Cancer Ther* 2004, 3(9):1101-1108.
14. Anand P, Sundaram C, Jhurani S, Kunnumakkara A B, Aggarwal B B: Curcumin and cancer: an "old-age" disease with an "age-old" solution. *Cancer Lett* 2008, 267(1):133-164.
15. Notarbartolo M, Poma P, Perri D, Dusonchet L, Cervello M, D'Alessandro N: Antitumor effects of curcumin, alone or in combination with cisplatin or doxorubicin, on human hepatic cancer cells. Analysis of their possible relationship to changes in NF-kB activation levels and in IAP gene expression. *Cancer Lett* 2005, 224(1):53-65.
16. Dujic J, Kippenberger S, Hoffmann S, Ramirez-Bosca A, Miguel J, Diaz-Alperi J, Bereiter-Hahn J, Kaufmann R, Bernd A: low concentrations of curcumin induce growth arrest and apoptosis in skin keratinocytes only in combination with UVA or visible light. *J Invest Dermatol* 2007, 127(8):1992-2000.
17. Anand P, Kunnumakkara A B, Newman R A, Aggarwal B B: Bioavailability of curcumin: problems and promises. *Mol Pharm* 2007, 4(6):807-818.
18. Garcea G, Berry D P, Jones D J, Singh R, Dennison A R, Farmer P B, Sharma R A, Steward W P, Gescher A J: Consumption of the putative chemopreventive agent curcumin by cancer patients: assessment of curcumin levels in the colorectum and their pharmacodynamic consequences. *Cancer Epidemiol Biomarkers Prey* 2005, 14(1):120-125.
19. Haraguchi N, Utsunomiya T, Inoue H, Tanaka F, Mimori K, Barnard G F, Mori M: Characterization of a side population of cancer cells from human gastrointestinal system. *Stem Cells* 2006, 24(3):506-513.
20. Ricci-Vitiani L, Lombardi D G, Pilozzi E, Biffoni M, Todaro M, Pesch le C, De Maria R: Identification and expansion of human colon-cancer-initiating cells. *Nature* 2007, 445(7123):111-115.
21. D'Angelo R C, Wicha M S: Stem cells in normal development and cancer. *Prog Mol Bioi Transl Sci* 2010, 95:113-158.
22. Visvader J E, Lindeman G J: Cancer stem cells in solid tumours: accumulating evidence and unresolved questions. *Nat Rev Cancer* 2008, 8(10):755-768.
23. Lobo N A, Shimono V, Qian D, Clarke M F: The biology of cancer stem cells. *Annu Rev Cell Dev Bioi* 2007, 23:675-699.
24. Al-Hajj M, Clarke M F: Self-renewal and solid tumor stem cells. *Oncogene* 2004, 23(43):7274-7282.
25. Awad O, Vustein J T, Shah P, Gul N, Katuri V, O'Neill A, Kong V, Brown M L, Toretsky J A, Loeb D M: High ALDH activity identifies chemotherapy-resistant Ewing's sarcoma stem cells that retain sensitivity to EWS-FLI1 inhibition. *PLoS One* 2010, 5(11):e13943.
26. Charafe-Jauffret E, Ginestier C, Iovino F, Tarpin C, Diebel M, Esterni B, Houvenaeghel G, Extra J M, Bertucci F, Jacquemier J et al: Aldehyde dehydrogenase 1-positive cancer stem cells mediate metastasis and poor clinical outcome in inflammatory breast cancer. *Clin Cancer Res* 2010, 16(1):45-55.
27. Dean M, Fojo T, Bates 5: Tumour stem cells and drug resistance. *Nat Rev Cancer* 2005, 5(4):275-284.
28. Tang C, Ang B T, Pervaiz 5: Cancer stem cell: target for anti-cancer therapy. *FASEB J* 2007, 21(14):3777-3785.
29. Vu V, Kanwar 55, Patel B B, Nautiyal J, Sarkar F H, Majumdar A P: Elimination of Colon Cancer Stem-Like Cells by the Combination of Curcumin and FOLFOX. *Transl Oncol* 2009, 2(4):321328.
30. Honoki K, Fujii H, Kubo A, Kido A, Mori T, Tanaka V, Tsujiuchi T: Possible involvement of stem-like populations with elevated ALDH1 in sarcomas for chemotherapeutic drug resistance. *Oncol Rep* 2010, 24(2):501-505.
31. Moreb J S: Aldehyde dehydrogenase as a marker for stem cells. *Curr Stem Cell Res Ther* 2008, 3(4):237-246.
32. Brennan S K, Meade B, Wang~Merchant A A, Kowalski J, Matsui W: Mantle cell lymphoma activation enhances bortezomib sensitivity. *Blood* 2010, 116(20):4185-4191.
33. Sladek N E: Human aldehyde dehydrogenases: potential pathological, pharmacological, and toxicological impact. *J Biochem Mol Toxicol* 2003, 17(1):7-23.
34. Vasiliou V, Pappa A, Estey T: Role of human aldehyde dehydrogenases in endobiotic and xenobiotic metabolism. *Drug Metab Rev* 2004, 36(2):279-299.
35. Ginestier C, Hur M H, Charafe-Jauffret E, Monville F, Dutcher J, Brown M, Jacquemier J, Viens P, Kleer C G, Liu 5 et al: ALDH1 is a marker of normal and malignant human mammary stem cells and a predictor of poor clinical outcome. *Cell Stem Cell* 2007, 1(5):555-567.
36. Vasiliou V, Nebert D W: Analysis and update of the human aldehyde dehydrogenase (ALOH) gene family. *Hum Genomics* 2005, 2(2):138-143.
37. Deng 5, Vang X, Lassus H, Liang 5, Kaur 5, Ve~Li C, Wang L P, Roby K F, Orsulic 5 et al: Distinct expression levels and patterns of stem cell marker, aldehyde dehydrogenase isoform 1 (ALOH1), in human epithelial cancers. *PLoS One* 2010, 5(4):e10277.
38. Franzmann E J, Reategui E P, Pedroso F, Pernas F G, Karakullukcu B M, Carraway K L, Hamilton K, Singal R, Goodwin W J: Soluble CD44 is a potential marker for the early detection of head and neck cancer. *Cancer Epidemiol Biomarkers Prey* 2007, 16(7):1348-1355.
39. Al-Hajj M, Wicha M S, Benito-Hernandez A, Morrison S J, Clarke M F: Prospective identification of tumorigenic breast cancer cells. *Proc Natl Acad Sci USA* 2003, 100(7): 3983-3988.
40. Prince M E, Sivanandan R, Kaczorowski A, Wolf G T, Kaplan M J, Dalerba P, Weissman I L, Clarke M F, Ailles L E: Identification of a sub population of cells with cancer stem cell properties in head and neck squamous cell carcinoma. *Proc Natl Acad Sci USA* 2007, 104(3):973-978.
41. Takaishi S, Okumura T, Tu S, Wang S S, Shibata W, Vigneshwaran R, Gordon S A, Shimada V, Wang T C: Identification of gastric cancer stem cells using the cell surface marker CD44. *Stem Cells* 2009, 27(5):1006-1020.
42. Liu V J, Van P S, Li J, Jia J F: Expression and significance of CD44s, CD44v6, and nm23 mRNA in human cancer. *World J Gastroenterol* 2005, 11(42):6601-6606.
43. Shimada V, Imamura M, Wagata T, Vamaguchi N, Tobe T: Characterization of 21 newly established esophageal cancer cell lines. *Cancer* 1992, 69(2):277-284.
44. Nakamura M: Establishment and characterization of a new human esophageal cancer cell line (YES-1). *Nippon Geka Hokan* 1991, 60(1):3-12.
45. Nakamura M, Murakami T, Sakata K, Kusanagi H, Saeki T, Uchisako H, Hayashi H, Tangoku A, Suzuki T: establishment and Characterization of a New Human Esophageal Cancer Cell Line (YES-2). *Bull Yamaguchi Med Sch* 1994, 41(3-4):149-153.
46. Nishihira T, Hashimoto V, Katayama M, Mori S, Kuroki T: Molecular and cellular features of esophageal cancer cells. *J Cancer Res Clin Onco/*1993, 119(8):441-449.
47. Mehlen P, Kretz-Remy C, Preville X, Arrigo A P: Human hsp27, *Drosophila* hsp27 and human alphaB-crystallin expression-mediated increase in glutathione is essential for the protective activity of these proteins against TNFalpha-induced cell death. *EMBO J* 1996, 15(11):2695-2706.
48. Jamasbi R J, Stoner G D, Foote U, Lankford T K, Davern S, Kennel S J: A monoclonal antibody to a carbohydrate epitope expressed on glycolipid and on alpha3beta1 integrin on human esophageal carcinoma. *Hybrid Hybridomics* 2003, 22(6):367-376.
49. Lingala S, Cui W, Chen X, Ruebner B H, Qian X F, Zern M A, Wu J: Immunohistochemical staining of cancer stem cell markers in hepatocellular carcinoma. *Exp Mol Patho/* 2010, 89(1):27-35.
50. van den Hoogen C, van der Horst G, Cheung H, Buijs J T, Lippitt J M, Guzman-Ramirez N, Hamdy F C, Eaton C L, Thalmann G N, Cecchini M G et al: High aldehyde dehydrogenase activity identifies tumor-initiating and metastasis-initiating cells in human prostate cancer. *Cancer research* 2010, 70(12):5163-5173.

51. Zhao J S, Li W J, Ge D, Zhang P J, Li J J, Lu C L, Ji X D, Guan D X, Gao H, Xu L V et al: Tumor initiating cells in esophageal squamous cell carcinomas express high levels of CD44. *PLoS ONE* 2011, 6(6):e21419.
52. Hartojo W, Silvers A L, Thomas D G, Seder C W, Lin L, Rao H, Wang Z, Greenson J K, Giordano T J, Orringer M B et al: Curcumin promotes apoptosis, increases chemosensitivity, and inhibits nuclear factor kappaB in esophageal adenocarcinoma. *Transl Oncol* 2010, 3(2):99-108.
53. O'Sullivan-Coyne G, O'Sullivan G C, O'Donovan T R, Piwocka K, McKenna S L: Curcumin induces apoptosis-independent death in oesophageal cancer cells. *Br J Cancer* 2009, 101(9):1585-1595.
54. Kang M R, Kim M S, Kim S S, Ahn C H, Voo N J, Lee S H: NF-kappaB signalling proteins p50/p105, p52/p100, RelA, and IKKepsilon are over-expressed in oesophageal squamous cell carcinomas. *Pathology* 2009, 41(7):622-625.
55. Tian F, Zang W D, Hou W H, Liu H T, Xue L X: Nuclear factor-kB signaling pathway constitutively activated in esophageal squamous cell carcinoma cell lines and inhibition of growth of cells by small interfering RNA. *Acta Biochim Biophys Sin (Shanghai)* 2006, 38(5):318-326.
56. Zhang Z, Ma J, Li N, Sun N, Wang C: Expression of nuclear factor-kappaB and its clinical significance in non-small-celliung cancer. *The Annals o/thoracic surgery* 2006, 82(1):243-248.
57. Yu H G, Vu L L, Yang V, Luo H S, Vu J P, Meier J J, Schrader H, Bastian A, Schmidt W E, Schmitz F: Increased expression of RelA/nuclear factor-kappa B protein correlates with colorectal tumorigenesis. *Oncology* 2003, 65(1):37-45.
58. Hatata T, Higaki K, Nanba E, Tatebe S, Ikeguchi M: Inhibition of nuclear factor-kappaB activity by small interfering RNA in esophageal squamous cell carcinoma cell lines. *Oncol Rep* 2011, 26(3):659-664.
59. Tanei T, Morimoto K, Shimazu K, Kim S J, Tanji V, Taguchi T, Tamaki V, Noguchi S: Association of breast cancer stem cells identified by aldehyde dehydrogenase 1 expression with resistance to sequential Paclitaxel and epirubicin-based chemotherapy for breast cancers. *Clin Cancer Res* 2009, 15(12):4234-4241.
60. Su Y, Qiu Q, Zhang X, Jiang 2, Leng Q, Liu Z, Stass S A, Jiang F: Aldehyde dehydrogenase 1 A1 positive cell population is enriched in tumor-initiating cells and associated with progression of bladder cancer. *Cancer Epidemiol Biomarkers Prev* 2010, 19(2):327-337.
61. Huang E H, Hynes M J, Zhang T, Ginestier C, Dontu G, Appelman H, Fields J Z, Wicha M S, Boman B M: Aldehyde dehydrogenase 1 is a marker for normal and malignant human colonic stem cells (SC) and tracks SC over-population during colon tumorigenesis. *Cancer Res* 2009, 69(8):3382-3389.
62. Murakami T, Nakamura M, Kusanagi H, Suzuki T: Establishment and characterization of human esophageal carcinoma celliines—especially the role of the serum-free culture). *Nihon Geka Gakkai zasshi* 1991, 92(11):1563-1570.
63. Douville J, Beaulieu R, Balicki D: ALOH1 as a functional marker of cancer stem and progenitor cells. *Stem Cells Dev* 2009, 18(1):17-25.
64. Lee H E, Kim J H, Kim V J, Choi S V, Kim S W, Kang E, Chung I V, Kim I A, Kim E J, Choi V et al.: An increase in cancer stem cell population after primary systemic therapy is a poor prognostic factor in breast cancer. *British journal of cancer* 2011, 104(11):1730-1738.
65. Rich I N: Cancer stem cells in radiation resistance. *Cancer research* 2007, 67(19):8980-8984.
66. Morrison R, Schleicher S M, Sun V, Niermann K J, Kim S, Spratt D E, Chung C H, Lu B: Targeting the mechanisms of resistance to chemotherapy and radiotherapy with the cancer stem cell hypothesis. *J Oncol* 2011, 2011:941876.
67. Batth B K, Tripathi R, Srinivas U K: Curcumin-induced differentiation of mouse embryonal carcinoma PCC4 cells. *Differentiation* 2001, 68(2-3):133-140.
68. Zhang S J, Ve F, Xie R F, Hu F, Wang B F, Wan F, Guo D S, Lei T: Comparative study on the stem cell phenotypes of C6 cells under different culture conditions. *Chin Med J (Engl)* 2011, 124(19):3118-3126.
69. Reuter S, Eifes S, Dicato M, Aggarwal B B, Diederich M: Modulation of anti-apoptotic and survival pathways by curcumin as a strategy to induce apoptosis in cancer cells. *Biochem Pharmaco/*2008, 76(11):1340-1351.
70. Zhang X Z, Li X J, Zhang H V: Curcumin's potential to modulate stem cell fate. *Trends Pharmacal Sci* 2009, 30(7):331-332.
71. Nautiyal J, Kanwar S S, Vu V, Majumdar A P: Combination of dasatinib and curcumin eliminates chemo-resistant colon cancer cells. *Journal of molecular signaling* 2011, 6:7.
72. Fong D, Veh A, Naftalovich R, Choi T H, Chan M M: Curcumin inhibits the side population (SP) phenotype of the rat C6 glioma cell line: towards targeting of cancer stem cells with phytochemicals. *Cancer Lett* 2010, 293(1):65-72.
73. Lim K J, Bisht S, Bar E E, Maitra A, Eberhart C G: A polymeric nanoparticle formulation of curcumin inhibits growth, clonogenicity and stem-like fraction in malignant brain tumors. *Cancer Biol Ther* 2011, 11(5):464-473.
74. Kanwar S S, Vu V, Nautiyal J, Patel B B, Padhye S, Sarkar F H, Majumdar A P: Oifluorinatedcurcumin (COF): a novel curcumin analog is a potent inhibitor of colon cancer stem-like cells. *Pharm Res* 2011, 28(4):827-838.

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A cell line selected, from an original population of cells, for the ability to survive a concentration of curcumin added to the culture medium, wherein the original population of cells are selected from the group consisting of: KY-5, YES-1, TE-1, KY-10, and YES-2.

2. The cell line of claim 1, wherein the concentration of curcumin is above or equal to 20 µM.

3. The cell line of claim 1, wherein the concentration of curcumin is above or equal to 40 µM.

4. The cell line of claim 1, wherein the concentration of curcumin is above or equal to 60 µM.

5. The cell line of claim 1, wherein the original population of cells are cancerous.

6. The cell line of claim 1, wherein the original population of cells are esophageal squamous cell carcinoma cells.

7. A kit comprising at least one cell line selected, from an original population of cells, for the ability to survive a concentration of curcumin added to the culture medium, wherein the original population of cells are selected from the group consisting of: KY-5, YES-1, TE-1, KY-10, and YES-2.

* * * * *